(12) United States Patent
Menchen et al.

(10) Patent No.: US 8,173,198 B2
(45) Date of Patent: May 8, 2012

(54) DEPOSITION OF METAL OXIDES ONTO SURFACES AS AN IMMOBILIZATION VEHICLE FOR CARBOXYLATED OR PHOPHATED PARTICLES OR POLYMERS

(75) Inventors: Steven M. Menchen, Fremont, CA (US); Christina E. Inman, San Mateo, CA (US); Meng Taing, Hayward, CA (US); George A. Fry, San Carlos, CA (US)

(73) Assignee: Life Technologies Corporation, Carlsbad, CA (US)

( * ) Notice: Subject to any disclaimer, the term of this patent is extended or adjusted under 35 U.S.C. 154(b) by 189 days.

(21) Appl. No.: 12/508,539

(22) Filed: Jul. 23, 2009

(65) Prior Publication Data
US 2010/0086927 A1  Apr. 8, 2010

Related U.S. Application Data

(60) Provisional application No. 61/083,145, filed on Jul. 23, 2008.

(51) Int. Cl.
*G01N 1/31* (2006.01)
*C23C 4/10* (2006.01)
*C12N 11/00* (2006.01)
*A61B 5/055* (2006.01)
*C07H 21/02* (2006.01)

(52) U.S. Cl. ....... 427/2.13; 427/453; 435/174; 530/810; 424/9.322; 536/23.1

(58) Field of Classification Search .................. 427/2.13, 427/453; 435/174; 530/810; 424/9.322; 536/23.1
See application file for complete search history.

(56) References Cited

U.S. PATENT DOCUMENTS

| 3,770,499 A | 11/1973 | Crowe et al. |
| 5,175,269 A | 12/1992 | Stavrianopoulos |
| 5,539,097 A | 7/1996 | Arnold, Jr. |

(Continued)

FOREIGN PATENT DOCUMENTS
CN   101568835   10/2009
(Continued)

OTHER PUBLICATIONS

Brovelli, et al., "Highly Oriented, Self-Assembled Alkanephosphate Monolayers on Tantalum(V) Oxide Surfaces", *Langmuir*, pp. 4324-4327 (1999).

(Continued)

*Primary Examiner* — Jezia Riley (57) ABSTRACT

Intermediates and methods for forming activated metal complexes bound to surfaces on oxide layers, immobilizing beads to the modified surface and articles produced thereby are described. Hydroxyl groups on the oxide surfaces are reacted with a metal reagent complex of the formula $Y(L\text{-}Pol)_m$, where Y is a transition metal, magnesium or aluminum, L is oxygen, sulfur, selenium or an amine, and "Pol" represents a passivating agent such as a methoxyethanol, a polyethylene glycol, a hydrocarbon, or a fluorocarbon. The resulting modified surface can be further reacted with a passivating agent having a phosphate functional group or a plurality of functional groups that are reactive with or that form complexes with Y. The metal oxide surfaces exhibit minimal binding to bio-molecules, exhibit uniform deposition and immobilization of beads at high density, can be subsequently modified to create surfaces having a variety of properties, and can be used for nucleic acid sequencing and other analyses and in single-molecule detection schemes.

19 Claims, 6 Drawing Sheets

U.S. PATENT DOCUMENTS

| | | | |
|---|---|---|---|
| 5,650,234 | A | 7/1997 | Dolence et al. |
| 5,750,341 | A | 5/1998 | Macevicz |
| 5,900,481 | A | 5/1999 | Lough et al. |
| 5,969,119 | A | 10/1999 | Macevicz |
| 6,093,370 | A | 7/2000 | Yasuda et al. |
| 6,133,436 | A | 10/2000 | Koster et al. |
| 6,146,767 | A | 11/2000 | Schwartz |
| 6,232,465 | B1 | 5/2001 | Hiatt et al. |
| 6,277,489 | B1 | 8/2001 | Abbot |
| 6,306,597 | B1 | 10/2001 | Macevicz et al. |
| 6,489,106 | B1 | 12/2002 | Shivashankar et al. |
| 6,645,644 | B1 | 11/2003 | Schwartz et al. |
| 6,664,079 | B2 | 12/2003 | Ju et al. |
| 6,811,980 | B2 | 11/2004 | Ford et al. |
| 6,830,886 | B1 | 12/2004 | Bosio et al. |
| 6,884,628 | B2 | 4/2005 | Hubbell |
| 7,057,026 | B2 | 6/2006 | Barnes et al. |
| 7,087,387 | B2 | 8/2006 | Gerdes et al. |
| 7,361,471 | B2 | 4/2008 | Gerdes et al. |
| 7,462,452 | B2 | 12/2008 | Williams et al. |
| 7,585,965 | B2 | 9/2009 | Scharnweber |
| 7,928,038 | B2 | 4/2011 | Menchen et al. |
| 2001/0029017 | A1 | 10/2001 | Yasuda et al. |
| 2002/0048771 | A1 | 4/2002 | Yasuda et al. |
| 2002/0055119 | A1 | 5/2002 | Yasuda et al. |
| 2002/0055146 | A1 | 5/2002 | Shivashankar et al. |
| 2002/0090641 | A1 | 7/2002 | Yasuda et al. |
| 2002/0132242 | A1 | 9/2002 | Gerdes et al. |
| 2002/0172963 | A1 | 11/2002 | Kelley et al. |
| 2003/0027328 | A1 | 2/2003 | Cunningham et al. |
| 2003/0082658 | A1 | 5/2003 | Mallet et al. |
| 2003/0143616 | A1 | 7/2003 | Kuimelis et al. |
| 2003/0148401 | A1 | 8/2003 | Agrawal et al. |
| 2004/0029162 | A1 | 2/2004 | Chaton et al. |
| 2004/0091925 | A1 | 5/2004 | Gerdes et al. |
| 2005/0003396 | A1 | 1/2005 | Ozkan et al. |
| 2005/0142296 | A1 | 6/2005 | Lakshmi |
| 2005/0266475 | A1 | 12/2005 | Chaton et al. |
| 2006/0035229 | A1 | 2/2006 | Scharnweber et al. |
| 2006/0194008 | A1* | 8/2006 | Schwartz et al. ............ 428/34.4 |
| 2006/0205007 | A1 | 9/2006 | Zhang et al. |
| 2006/0246225 | A1 | 11/2006 | Moritz et al. |
| 2007/0015223 | A1 | 1/2007 | Sanuki et al. |
| 2007/0098892 | A1 | 5/2007 | Chung et al. |
| 2007/0238679 | A1 | 10/2007 | Rank |
| 2008/0020214 | A1 | 1/2008 | Kawai et al. |
| 2008/0032301 | A1 | 2/2008 | Rank et al. |
| 2008/0044830 | A1 | 2/2008 | Tovar et al. |
| 2008/0132429 | A1 | 6/2008 | Perov et al. |
| 2008/0153100 | A1 | 6/2008 | Rank et al. |
| 2008/0274671 | A1 | 11/2008 | O'Donoghue et al. |
| 2009/0011949 | A1 | 1/2009 | Hogan et al. |
| 2009/0082225 | A1 | 3/2009 | Gerdes et al. |
| 2009/0099027 | A1 | 4/2009 | Greiner et al. |
| 2009/0156426 | A1 | 6/2009 | Schiestel et al. |
| 2009/0197777 | A1 | 8/2009 | Chagovetz et al. |

FOREIGN PATENT DOCUMENTS

| | | |
|---|---|---|
| EP | 0730168 | 9/2003 |
| EP | 1034430 | 2/2006 |
| EP | 1637613 | 3/2006 |
| EP | 1192448 | 9/2006 |
| EP | 2011898 | 1/2009 |
| EP | 2138462 | 12/2009 |
| WO | 99/30159 | 6/1999 |
| WO | 99/54718 | 10/1999 |
| WO | 01/02839 | 1/2001 |
| WO | 01/50131 | 7/2001 |
| WO | 02/20873 | 3/2002 |
| WO | 03/076903 | 9/2003 |
| WO | 2004/011672 | 2/2004 |
| WO | 2004/023128 | 3/2004 |
| WO | 2005/103226 | 11/2005 |
| WO | 2006/058237 | 6/2006 |
| WO | 2006/068619 | 6/2006 |
| WO | 2006/084132 | 8/2006 |
| WO | 2008/033867 | 3/2008 |
| WO | 2008/039998 | 4/2008 |
| WO | 2008/043551 | 4/2008 |
| WO | 2008/063134 | 5/2008 |
| WO | 2009/004117 | 1/2009 |
| WO | 2009/026546 | 2/2009 |
| WO | 2009/129410 | 10/2009 |

OTHER PUBLICATIONS

Chaix, C. et al., "Oligonucleotide synthesis on maleic anhydride copolymers covalently bound to silica spherical support and characterization of the obtained conjugates", *J Applied Polymer*, vol. 70, XP002505585, pp. 2487-2497 (1998).

Danahy, et al., "Self-Assembled Monolayers of alpha-oo-Diphosphonic Acids on Ti Enable Complete or Spatially Controlled Surface Derivation", *Langmuir*, pp. 5333-5337 (2004).

Database WPI, "Week 200652", Thomson Scientific, 2006-506068; XP002492928; & JP 2006 177914 Abstract, Jul. 6, 2006.

Filippov, A et al., "Discrimination of the saturated vapours of alcohols by the responses of assembly of piezoquartz sensors overed with metal stearates and their complexes with octadecylamine", *Semiconductor Physics, Quantum Electronics & Optoelectronics*, vol. 9(2), pp. 87-91 (2006).

Filippov, A. et al., "New coating materials for hydrocarbon discrimination using a multisensor system and gas chromatography", *Theoretical and Experimental Chemistry*, vol. 41, No. 6, pp. 389-394 (2005).

Folkers, et al., "Self-Assembled Monolayers of Long-Chain Hydroxamic Acids on the Native Oxides of Metals", *Langmuir*, pp. 813-824 (1995).

Frey, et al., "Peptomer Aluminum Oxide Nanoparticle Conjugates as Systemic and Mucosal Vaccine Candidates: Synthesis and Characterization of a Conjugate Derived from the C4 Domain of HIV-1mn Gp120", *Bioconjugate Chem.*, pp. 424-433 (1997).

Gao, et al., "Order-Disorder Transitions in Self-Assembled Monolayers: A 13C Solid-State NMR Study", *Langmuir*, pp. 115-118 (1997).

Gao, et al., "Self-Assembled Monolayers of Alkylphosphonic Acids on Metal Oxides", *Langmuir*, pp. 6429-6435 (1996).

Guo, et al. "Direct Fluorescence Analysis of Genetic Polymorphisms by Hybridization with Oligonucleotide Arrays on Glass Supports,", *Nucleic Acids Res*, vol. 22, pp. 5456-5465 (1994).

Hanson, et al. "Bonding Self-Assembled, Compact Organophosphonate Monolayers to the Native Oxide Surface of Silicon", *JACS Articles*, pp. 16074-16080 (2003).

Hofer, et al., "Alkyl Phosphate Monolayers, Self-Assembled from Aqueous Solution onto Metal Oxide Surfaces", *Langmuir*, pp. 4014-4020 (2001).

Jon, et al., "Construction of Nonbiofouling Surfaces by Polymeric Self-Assembled Monolayers", *Langmuir*, pp. 9989-9993 (2003).

Midwood, et al., "Easy and Efficient Bonding of Biomolecules to an Oxide Surface of Silicon", *Langmuir*, pp. 5501-5505 (2004).

Molecular Probes, "Aminoallyl dUTP product information", (,access online at probes.invitrogen.com/media/pis/mp21664.pdf), 4 pages (2004).

PCT/US2008/074075 International Preliminary Report on Patentability.

PCT/US2008/074075 International Search Report.

PCT/US2007/085347 International Preliminary Report Patentability.

PCT/US2007/085347 International Search Report.

PCT/US2007/085347 Written Opinion.

Silverman, et al, "Comparative Properties of Siloxane vs. Phosphonate Monolayers on A Key Titanium Alloy", *Langmuir*, pp. 225-228 (2005).

Span, et al, "Surface Modification of Indium Tin Oxide by Phenoxytin Complexes", *Langmuir*, pp. 948-952 (2001).

Textor, et al, "Structural Chemistry of Self-Assembled Monolayers of Octadecylphosphoric Acid on Tantalum Oxide Surfaces", *Langmuir*, pp. 3257-3271 (2000).

Tosatti, et al, "Self-Assembled Monolayers of Dodecyl and Hydroxydodecyl Phosphates on Both Smooth and Rough Titanium and Titanium Oxide Surfaces", *Langmuir*, pp. 3537-3548 (2002).

Wong, S., "Chemistry of Protein Conjugation and Cross-Linking", CRC Press, pp. 87-89; 99-101 (1991).

\* cited by examiner

FIG. 1

X = C, Si, Al, and
Transition metals
n = 1 to 5

FIG. 2

$$Y(OR_6)_m + mPol\text{-}LH \longrightarrow Y(L\text{-}Pol)_m + mR_6\text{-}OH$$

Y = Si, Ta, Ti, Nb, Zr, Al, Hf $R_6$ = $C_1$-$C_5$ hydrocarbon

L = oxygen, sulfur, selenium, amine

Pol = methoxyethanol, PEG, substituted PEG, hydrocarbon, substituted hydrocarbon, fluorocarbon, substituted fluorocarbon m = an integer

X = C, Si, Al, transition metal

Y = Si, Ta, Ti, Nb, Zr, Hf, Al

Pol = methoxyethanol, PEG, substituted PEG, hydrocarbon, substituted hydrocarbon, fluorocarbon, substituted fluorocarbon
n = 1 to 5

FIG. 6A

DNA coated polystyrene beads attached to a zirconium coated glass slide.

FIG. 6B

DNA coated polystyrene beads attached to a zirconium coated cyclic olefin polymer slide

DEPOSITION OF METAL OXIDES ONTO SURFACES AS AN IMMOBILIZATION VEHICLE FOR CARBOXYLATED OR PHOPHATED PARTICLES OR POLYMERS

BACKGROUND

1. Technical Field

This application relates generally to surface modification techniques and, in particular, to the attachment and immobilization of oligonucleotide-labeled beads on oxide layers and to articles produced thereby.

2. Background of the Technology

Nucleic acid sequencing requires the interrogation of individual incorporation events by polymerases, preferably on surfaces. Generally, these incorporation events are identified by examination of labels on the incorporated nucleotides as individual molecules (i.e., single molecule detection). The most popular labels are fluorescent dyes. Even rare non-specific adsorption of labeled nucleotides on the surfaces creates false signals. Therefore, binding of the substrates to the surfaces should be minimized.

There still exists a need for improved workflows and control of the surface activation chemistry and stability of bead attachment substrates which would result in surfaces exhibiting minimal absorption of biomolecules.

SUMMARY

The current application discloses novel methods of immobilizing a particle on to a surface performed by depositing a metal oxide layer onto the surface; and contacting a functionalized particle onto the metal oxide surface wherein the particle is immobilized on the surface. The functionalized particle includes phosphated moieties, carboxylated moieties or a combination thereof and the phosphated moieties are derived from phosphodiester linkages selected from the group consisting of a nucleic acid, an oligonucleotide or a biomolecule containing nucleic acids, carboxylates, phosphonates or phosphates. The particle is selected from a bead, a refractory bead or a ligation bead and is composed of a material selected from the group consisting of organic polymers, silicate polymers, alumina, titania, zirconia, and combinations thereof while the surface is a glass, a metal, a metal oxide or an organic polymer. The polymer is selected from the group including cyclic olefin polymer (COP), cyclic olefin co-polymer (COC), polypropylene, polycarbonate, fluorinated polyethylene, polymethyl methacrylate, polystyrene, polybutadiene, and blends thereof including a blended mixture of polystyrene, polypropylene and polybutadiene. The polymer can be a solid at operating temperatures, optically transparent, stable in a variety of solvents and can be activated to comprise transition metal reactive groups.

The reactive group includes hydroxyl, carboxyl, phosphate, phosphonate, silanol, alumina and oxides of transition metals and the surface comprises a material selected from silicon, aluminum, germanium, gallium, titanium, tantalum, indium, zirconium, magnesium, tin, gold, silver, hathium, carbon and an organic polymer derivative.

The method of immobilization can include a passivation step including a passivating agent selected from the group consisting of poly(vinyl phosphoric acid), pyrophosphate, poly(acrylic acid), polyvinyl alcohol), polyethylene glycol comprising functionalities of poly-phosphate-, poly-carboxylate-, or poly-hydroxyl- or combinations thereof and poly(N,N-dimethylacrylamide).

In yet another embodiment disclose is a method of making a particle immobilized on a surface comprising: layering an organic soluble metal complex on the surface, forming a functionalized metal complex surface; hydrolyzing the functionalized metal complex; contacting a particle to the metal complex layer, wherein the bead is immobilized to the surface. The method can further include passivating the surface with the agents listed above. The method can also include pre-treating the surface prior to layering the surface with the metal complex, wherein pre-treating comprises treating the surface with an oxygen plasma or contacting the surface with tetrabutyl ammonium hydroxide, chromic acid in sulfuric acid, potassium hydroxide in methanol, hydrogen peroxide in sulfuric acid, nitric acid in sulfuric acid, hydrogen peroxide in ammonia, sulfuric acid, hydrofluoric acid, EDTA, or combinations thereof.

In certain embodiments a compound of the formula:

wherein Y is silicon, aluminum, germanium, gallium, titanium, tantalum, indium, hafnium, zirconium, magnesium, tin, gold, silver or another transition metal; L is oxygen, sulfur, selenium or an amine; each "Pol" group independently represents a methoxyethanol, polyethylene glycol, a substituted polyethylene glycol, a hydrocarbon, as substituted hydrocarbon, a fluorocarbon or a substituted fluorocarbon, and m is an integer. Y is selected from the group consisting of Ta, Ti, Zr, and Al. Y can also be contacted with a plurality of functional groups that are reactive with Y or that form complexes with Y and include: hydroxyl groups, amine groups, phosphate groups, phosphonate groups, thiol groups, alkylphosphate groups, carboxyl groups and combinations thereof.

In another embodiment, a solid support having a surface treated with a multivalent passivating agent comprising: a metal oxide layer; at least one functionalized particle in contact with the metal oxide layer; and the passivating agent in contact with the metal oxide layer, wherein the surface is passivated with a passivating agent. The surface comprises a substrate comprising a glass, a metal, a metal oxide or an organic polymer and the functionalized particle comprises phosphated moieties, carboxylated moieties or a combination thereof. The solid support can have phosphated moieties derived from phosphodiester linkages selected from the group consisting of a nucleic acid, an oligonucleotide or a biomolecule containing nucleic acids, carboxylates, phosphonates or phosphates and a passivating agent selected from the group consisting of polyvinyl phosphoric acid), pyrophosphate, poly(acrylic acid), polyvinyl alcohol), polyethylene glycol comprising functionalities of poly-phosphate-, poly-carboxylate-, or poly-hydroxyl- or combinations thereof, and poly(N,N-dimethylacrylamide).

In one embodiment the particle is at least 0.5 to 10 microns in size and includes an attached nucleic acid, oligonucleotide or primer.

In another embodiment, a surface of a substrate comprising a nucleic acid coated immobilized bead is formed by the process of applying a metal oxide layer; binding at least one functionalized nucleic acid coated bead with the metal oxide layer; wherein the at least one nucleic acid coated bead is immobilized to the surface. The surface can comprises a substrate comprising a glass, a metal, a metal oxide or an organic polymer. The immobilized bead can include a functionalized nucleic acid coated bead having phosphated moieties, carboxylated moieties or a combination thereof and the phosphated moieties are derived from phosphodiester linkages selected from the group consisting of a nucleic acid, an oligonucleotide or a biomolecule containing nucleic acids, carboxylates, phosphonates or phosphates. The surface can optionally comprising a passivating agent subsequent to the binding of the at least one functionalized nucleic acid coated bead and the passivating comprises a passivating agent selected from the group consisting of poly(vinyl phosphoric acid), pyrophosphate, poly(acrylic acid), poly(vinyl alcohol), polyethylene glycol comprising functionalities of poly-phosphate-, poly-carboxylate-, or poly-hydroxyl- or combinations thereof, and poly(N,N-dimethylacrylamide).

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

A technique for forming very thin layers of aluminum or, transition metal compounds (e.g., esters) onto oxide (e.g., silica), glass, metal or polymer surfaces, with the object of creating a surface that will immobilize phosphated or carboxylated particles, polymers or passivating agents, is provided. The technique can be applied to the immobilization of nucleic acid-laden beads, in preparation for nucleic acid sequencing or other analyses, onto a glass microscope slide surface, and other surfaces known to one of skill in the art such as a metal, a metal alloy, silica, polymer, a copolymer and the like and combinations and derivatives thereof, modified with aluminum or transition metal oxides. The technique includes the step of hydrolyzing the metal-treated surface to create the metal-oxide immobilizing surface by treating the metal-treated substrate with water. Passivation of the oxide surface subsequent to bead immobilization to prevent nonspecific binding onto the slide of reagents used in nucleic acid sequencing or single molecule-detection methods. Such reagents include enzymes and dye-labeled oligonucleotides. The passivating agent used to treat the metal-treated slide are phosphate, phosphonate or carboxylate containing passivation agents such as poly(vinyl phosphoric acid), pyrophosphate, poly(acrylic acid), polyethylene glycol comprising functionalities of poly-phosphate, poly-carboxylate, or poly-hydroxyl- or combinations thereof, and the like, as well as non-ionic polymeric materials known to absorb to glass surfaces such as poly(vinyl alcohol) and poly(N,N-dimethylacrylamide).

Transition metal esters of Ta(5+), Ti(4+), and Zr(4+) are commercially available (e.g., as methyl, ethyl, and isopropyl esters). However, the reactivity of these esters with trace amounts of water to produce insoluble oxides precludes their use in an aqueous environment for coating surfaces. In addition, their limited solubility in organic solvents, especially the commercially available esters of Ti(4+), precludes the use of these reagents in many organic solvents.

The present inventors have found that the commercial esters of Al(3+), Zr(4+), Ti(4+) and Ta(5+) can be reacted with 1 or more equivalents of methoxyethanol (or higher molecular weight mono-methoxy polyethylene glycol oligomers) to create a solution of a methoxy-ethanol activated metal complex, and with the capability of forming very thin layers of those metals on oxide surfaces such as silica surfaces, in a very reproducible manner. The added step of hydrolyzing the metal-treated surface creates a metal-oxide immobilizing surface. Following hydrolysis and immobilization of the bead, the surface can be passivated such that it is suitable for use in nucleic acid sequencing and single-molecule detection schemes as described in U.S. patent application Ser. No. 11/345,979 by McKernan et al., filed Feb. 1, 2006 and U.S. patent application Ser. No. 11/737,308 by K. J. McKernan et al., filed Apr. 19, 2007, incorporated herein by reference in its entirety for all purposes.

Some aspects of the present teachings make use of surface modification and passivation techniques which have been described in U.S. patent application Ser. No. 11/943,851, filed Nov. 21, 2007, entitled "Intermediates and Methods for Forming Passivated Surfaces on Oxide Layers and Articles Produced Thereby", incorporated herein by reference in its entirety for all purposes.

The overall scheme is summarized in FIGS. 1-5.

Figure 1:
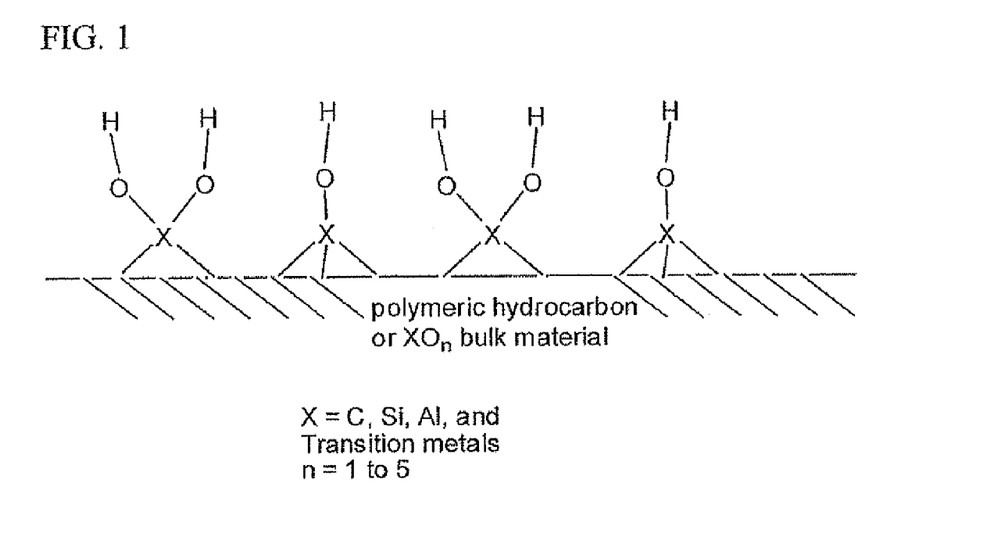
FIG. 1 is a schematic depicting an oxide surface comprising hydroxyl groups which can be passivated according to one embodiment.

FIG. 1A is a schematic depiction of the oxide surface of a refractory material (e.g., silicate glass, quartz or crystalline hydrocarbon polymers) which contains reactive hydroxyl groups. Hydroxyl groups on the surface can be converted to hydroxide anions by treatment with a base.

The surface can be treated prior to activation with an oxide layer, with an oxygen plasma or with tetrabutyl ammonium hydroxide, potassium hydroxide in methanol, hydrogen peroxide in sulfuric acid (i.e., "piranha" solution), nitric acid in sulfuric acid (i.e., "aquaregia"), hydrogen peroxide in ammonia (i.e., "RCA" solution), sulfuric acid, hydrofluoric acid, EDTA, or successive combinations of these treatments.

Figure 2:
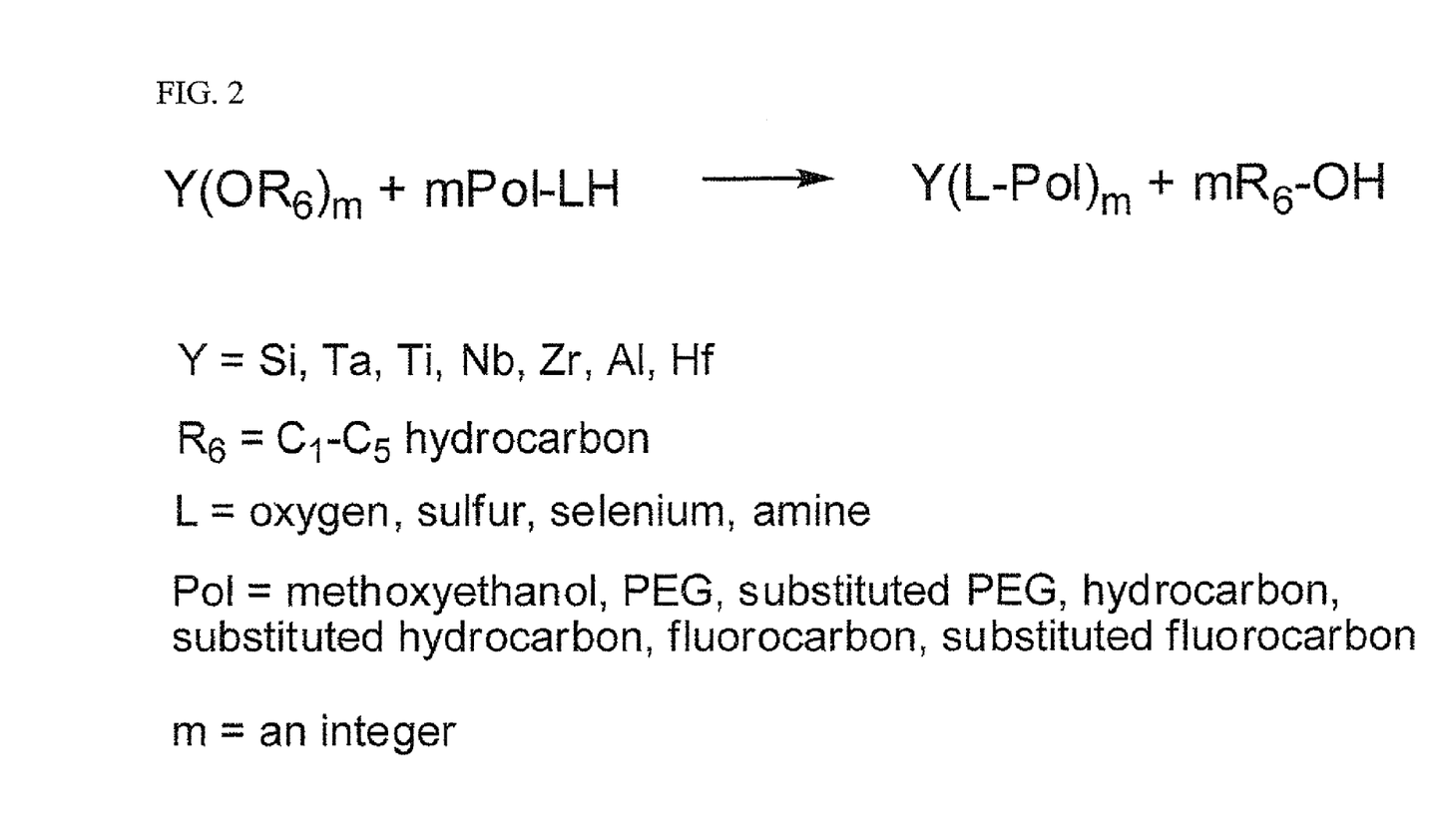
FIG. 2 shows the preparation of a metal reagent which can be used to modify oxide surfaces.

FIG. 2 illustrates the preparation of a metal reagent which can be used to modify oxide surfaces. In order to synthesize the reagent, more than the number of required equivalents (i.e., m) of the Pol-LH compound can be added to get total replacement of the low molecular weight alcohols on the metal. As an example, methoxyethanol is mixed with the metal ester to yield a solution of methoxy-ethanol activated metal ester complex. To create the transition metal oxide modified surface, the substrate is soaked in a solution of the methoxy ethanol activated metal ester complex for several hours to overnight. Once removed from the solution and cleaned free of reagent, the slide is soaked in deionized water to drive the hydrolysis of remaining methoxy ethanol groups.

Figure 3:
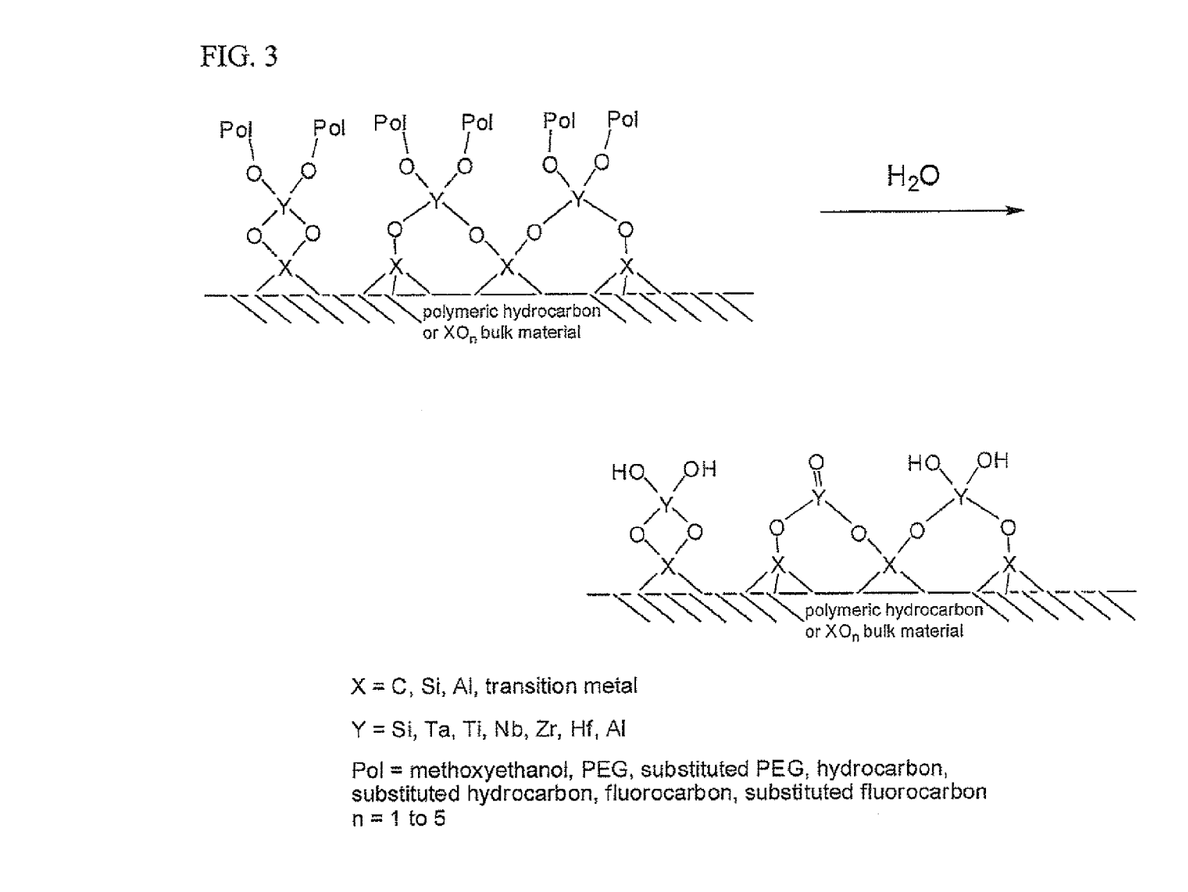
FIG. 3 shows a modified surface resulting from the reaction of metal esters of a metal reagent compound with the oxide surface followed by hydrolysis to create an activated metal oxide surface.

FIG. 3 shows the result of the hydrolysis of the metal reagent complex with the oxide surface. In principle, residual "Pol" (e.g., methoxyethanol) groups are removed from the surface through hydrolysis. This results in a surface available for immobilization of nucleic acid beads containing targeted sequences to be analyzed and subsequent binding with surface passivating agents. It has been found that modification of the surface with the metal reagent results in a very thin layer of metal oxide (as demonstrated by elemental analysis at the surface by X-Ray Photo-detection Spectroscopy (XPS)) under a variety of conditions. In addition, the surfaces can be formed under very mild conditions. The metal reagents are also easy to make and require no purification prior to use. The surface, following bead immobilization, is ready to use for nucleic acid sequencing and single-molecule detection schemes or can be further modified with an additional reagent to further passivate the surface.

Figure 4:
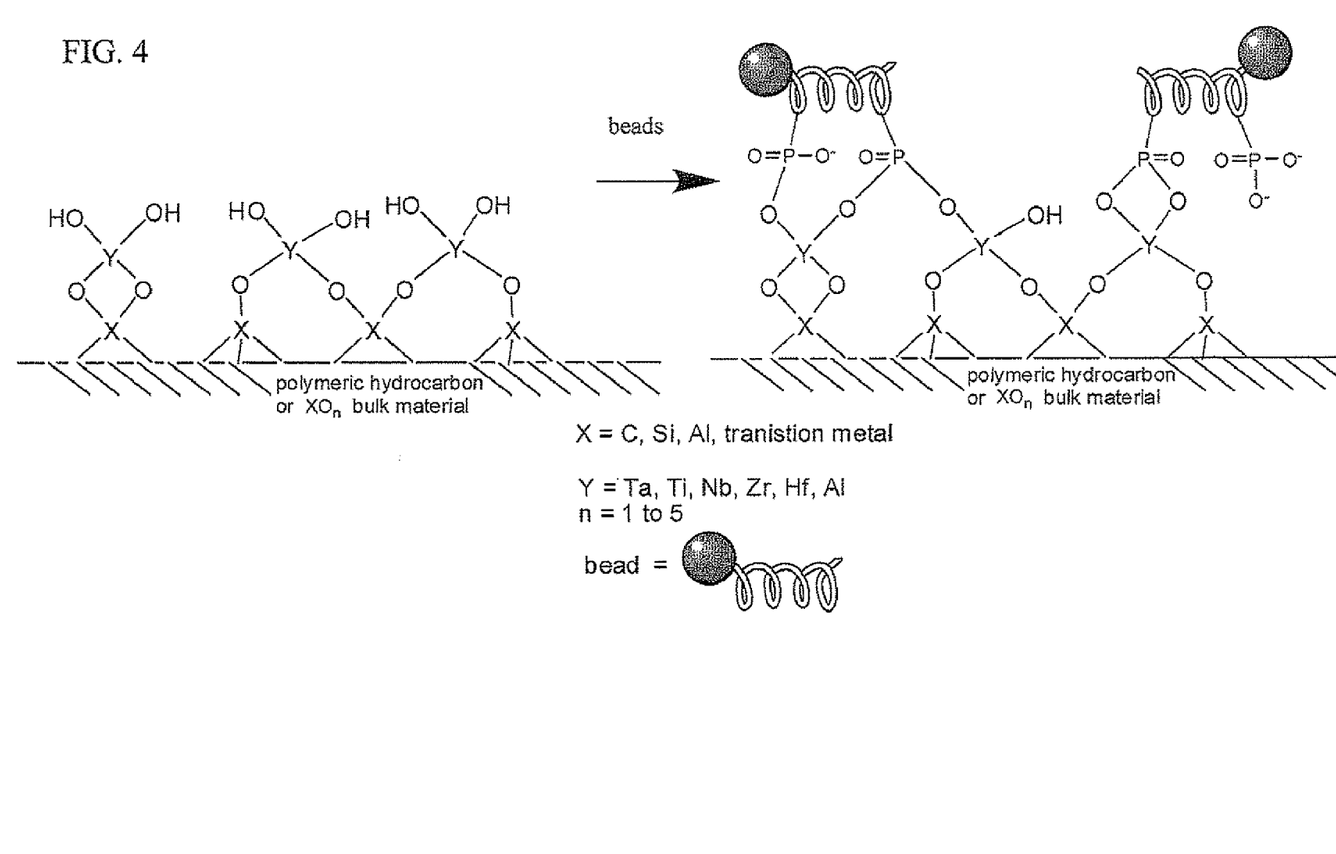
FIG. 4 illustrates the binding of nucleic acid ligation beads to an activated metal oxide surface via phosphate groups.

FIG. 4 shows the binding of nucleic acid coated beads to an activated metal oxide surface via poly-phosphate groups present in the phosphodiester bonds joining the deoxyribonucleotides found within the oligonucleotides attached to the bead. The orientation of the numerous oligonucleotides attached to the surface of the bead is such that only a very few oligonucleotides are involved in the actual bead attachment to the substrate surface, leaving the majority available for analyses. This bead immobilization scheme eliminates the need for a bead pre-activation step following ePCR for immobilization.

Figure 5:
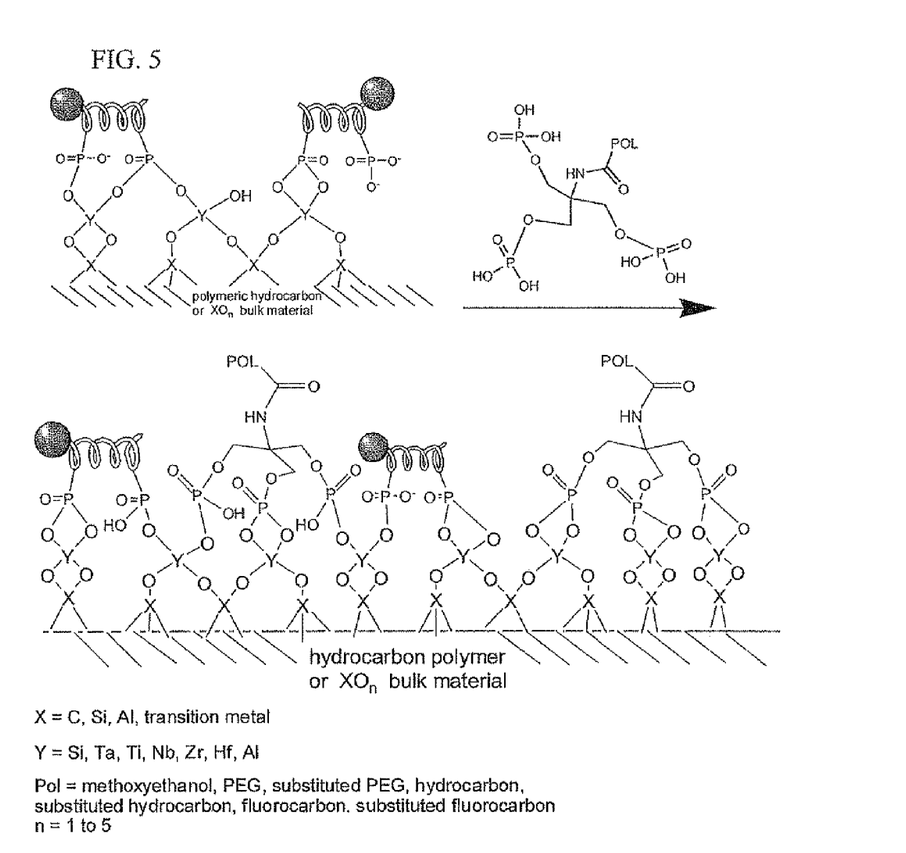
FIG. 5 is a schematic showing the result of the interaction of a metal reagent treated surface with a multivalent poly (ethylene glycol) (PEG) passivating agent comprising a plurality of phosphate groups subsequent to bead immobilization.

The oxide surface can be treated with a passivating agent contain multiple phosphate, carboxylate or phosphonate groups and combinations thereof, wherein the oxide surface has been previously treated with a metal reagent complex. FIG. 5 is a schematic showing the passivating of the metal reagent treated surface with a multivalent PEG passivating agent comprising a plurality of phosphate groups subsequent to bead immobilization.

The use of a metal reagent pre-layer and a phosphate functional passivating agent following bead immobilization enables the use of readily available phosphate, phosphonate or carboxylate functionalities for the creation of a surface with a variety of properties. Phosphates can be readily synthesized from phosphorous oxychloride and the alcohol versions of the passivating agents.

The use of metal reagents and phosphate, carboxylate and/or phosphonate functional passivating agents also enables the creation of a variety of surface types and properties by formulating e.g., phosphate esters with different polymeric groups. For example, phosphates of hydrocarbon, fluorocarbon, and PEG alcohols could be mixed together prior to contact with the metal-reagent treated oxide surface to obtain a modified surface with desirable properties for a specific application. In addition, a phosphate ester containing a specific functionality (e.g., biotin) could be used to obtain a surface that would bind another molecule (e.g., streptavidin).

According to some embodiment's, the polyvalent reagent can be represented by the following formula:

wherein n is a positive integer. For example, n can be 3 to 100.

A solid support having a surface treated with a multivalent passivating agent is also provided. According to some embodiments, a solid support is provided which comprises: an oxide layer comprising an oxide of carbon, silicon, aluminum, germanium, gallium, titanium, tantalum, indium, zirconium, magnesium, tin, gold, silver, or other transition metals; atoms of a metal selected from the group consisting of silicon, a transition metal, magnesium and aluminum bonded to the oxide layer; and a passivating reagent comprising a passivating moiety selected from the group consisting of a methoxyethanol, a substituted polyethylene glycol, an unsubstituted polyethylene glycol, a hydrocarbon, a substituted hydrocarbon, a fluorocarbon and a substituted fluorocarbon; wherein the passivating reagent is covalently bonded to or forms a complex with one or more atoms of the metal at a plurality of locations.

As set forth above, modification of a surface with metal esters enables very controlled, very thin layer deposition of a metal precursor to a variety of oxide surfaces under very mild conditions. The metal esters are very easy to make, and require no purification prior to use (although purification can be performed in some embodiments). The use of a combination of metal ester deposition followed by hydrolysis and then multivalent passivating agent deposition (following bead deposition) can enable the creation of a variety of surfaces types and properties. For example, the surface can be treated with a multivalent passivating agent having different functional groups during the final surface modification.

Synthesis of Multivalent Passivating Agents Comprising Phosphate Moieties

The multivalent passivating agent can be readily synthesized using known chemical synthesis techniques. A method for synthesizing a multivalent passivating agent comprising a polyethylene glycol passivating moiety and a plurality of phosphate moieties is described below. The phosphate moieties are capable of forming complexes with metal atoms on a support surface.

Synthesis and Column Purification of mPEG2K Acetamido-Tris-Alcohol

The Methyl PEG2K-Acetic Acid intermediate reaction product can then be reacted with 2-amino-2-(hydroxymethyl) propane-1,3-diol as set forth below to form a second intermediate comprising a plurality of hydroxyl groups (i.e., an mPEG2K Acetamido-Tris-Alcohol).

Average Molecular weight 2000: 2070 plus/minus (44)n

Average Molecular weight 2000: 2173 plus/minus (44)n

This procedure is described below,

1) Methyl PEG$_{2000}$-acetic acid (12 gram, av. 0.006 mole) was co-evaporated with anhydrous toluene and acetonitrile, respectively three times (30 ml each) and re-dissolved in dry dichloromethane (10 ml). Triethylamine (TEA) (0.75 ml, 0.006 mole) was added under dry nitrogen. Disuccinimidyl carbonate (DSC) (3 gram, 0.012 moles) was added portion-wise under nitrogen with stirring. The reaction was left at room temperature for 4 hours and the solvent was removed on a rotary evaporator. Anhydrous dioxane (10 ml) was added to dissolve the residue, and the solution added dropwise to a saturated trishydroxymethylaminomethane (Tris base) aqueous solution with vigorous stirring. The reaction was left for two hours at room temperature and then extracted with DCM (total 100 ml) three times. The DCM phase was dried with sodium sulfate and an oil crude was obtained after removal of solvent.

2) The residue was purified on a silica gel (100 ml) column packaged in 5% MeOH-DCM and eluted with 5% MeOH-DCM. Fractions 12-20 were identified as the desired product (9.5 gram) by MALDI-MS and proton nuclear magnetic resonance spectroscopy (HNMR). Yield was 76%.

3) $R_f$ value of the product was about 0.5 in 10% MeOH-DCM on a silica TLC plate.

Synthesis and Purification of Methyl PEG-2K Acetamido-Tris-Triphosphate

The mPEG$_{2000}$ Acetamido-Tris-Alcohol intermediate can then be reacted with bis(2-cyanoethyl)di-isopropylphosphoramidite as set forth below to form the multivalent passivating agent.

-continued

This procedure is described below.

1) mPEG2K acetamido-Tris-alcohol (2.2 gram, 1 mM) was coevaporated with anhydrous toluene and acetonitrile, respectively, three times (30 ml each). Bis(2-cyanoethyl) di-isopropylphosphoramidite (FW=271.6, 1.22 g, 4.5 mM) and tetrazole-acetonitrile solution (15 ml, 0.45M, 6.75 mM) were added under nitrogen. The reaction mixture was stirred at room temperature for 3 hours. Tert-Butyl hydroperoxide (70% aqueous, 6 ml, 45 mM) was added and the mixture was stirred at room temperature for 2 hours. The solvent was removed on a rotary evaporator. The residue was extracted with DCM three times and washed with sodium bicarbonate buffer (pH 9) and dried over sodium sulfate. The residue was silica gel column purified with eluent 10% methanol in DCM. Fractions 15-20 were identified as the desired product by MS and HNMR.

2) $R_f$ of the product was 0.55 in 10% MeOH-DCM on a silica TLC plate.

3) The purified phosphonate ester was placed in $NH_3.H_2O$ (5 ml) and incubated overnight at room temperature. The ammonia was removed under vacuum, re-dissolved in water and purified on Sephadex DEAE A-25 column (equilibrated with 2M potassium bicarbonate and washed thoroughly with water). The phosphate was eluted with 2M triethylamine acetate buffer. The buffer was removed by repeatedly co-evaporating with water under vacuum and the product (1.7 gram) was characterized by MALDI-MS, proton NMR and phosphor NMR. Yield was 70%.

Experimental

Aspects of the present teachings may be further understood in light of the following examples, which should not be construed as limiting the scope of the present teachings in any way.

Surfaces Treated With Metal Reagent Complexes

XPS data are shown in the table below for a methoxy-ethanol activated zirconium complex modified glass surface after performing the following manipulations on the surface. In this example, a plasma cleaned glass slide was soaked in a methoxy-ethanol activated zirconium complex solution overnight followed by rinsing the slide first with methoxy-ethanol and then with water, followed by drying the slide. The slide was then annealed at 150° C. for four hours.

| Element | Atomic % |
| --- | --- |
| Oxygen | 54 |
| Zirconium | 3 |
| Silicon | 23 |
| Carbon | 20 |

Figure 6A:
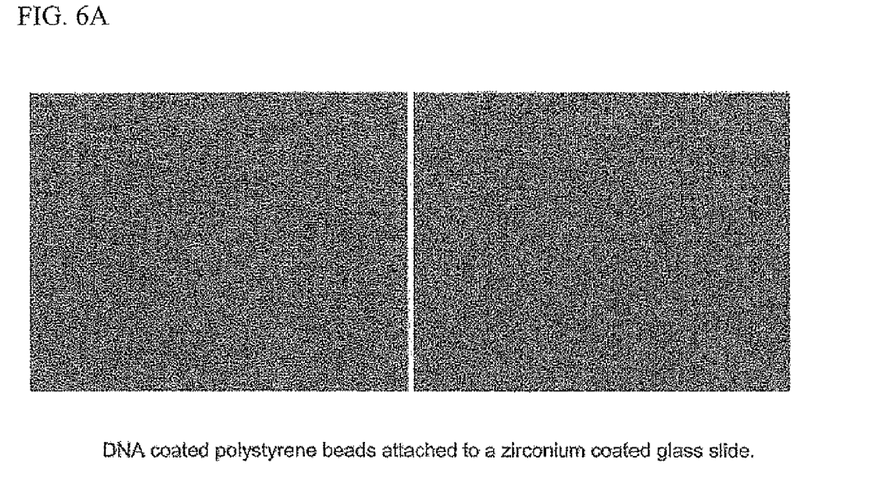
FIGS. 6A and 6B are photographs from two areas of a slide showing nucleic acid coated polystyrene beads bind immobilized on either a zirconium treated glass surface (FIG. 6A) or a COP surface (FIG. 6B).

Nucleic acid coated polystyrene beads (following emulsion PCR (ePCR) and enrichment) were shown to bind in high density on the resulting zirconium surface (see FIG. 6A, two separate fields of the same slide indicating surprisingly uniform deposition, deposition on a single plain and immobilization of the beads). The metal oxide modified surface can be subsequently modified with a passivating agent while still maintaining the integrity of the zirconium layer.

XPS data are shown in the table below for a methoxy-ethanol activated zirconium complex modified surface that was soaked for four hours in a 1% solution of polyvinyl phosphoric acid).

| Element | Atomic % |
| --- | --- |
| Oxygen | 52 |
| Zirconium | 2 |
| Silicon | 17 |
| Carbon | 24 |
| Phosphorus | 2 |

The data demonstrate that it was possible to passivate the surface to prevent non-specific binding of dye-labeled oligonucleotides during high-throughput sequencing (e.g., nucleic acid sequencing by ligation and single molecule sequencing) procedures.

XPS data are shown in the table below for a methoxy-ethanol activated zirconium complex modified cyclic olefin polymer (COP) slide surface. To modify the COP slide, zirconium ethoxide (1 gm) is mixed with 100 mL methoxy ethanol to yield a solution of the methoxy-ethanol activated zirconium complex. The cyclic olefin polymer (COP) slide was oxygen plasma cleaned (300 watts, 5 minutes, 150 mtorr $O_2$), rinsed with water and dried under vacuum.

| Element | Atomic % |
| --- | --- |
| Oxygen | 34 |
| Zirconium | 4 |
| Carbon | 62 |

Figure 6B:
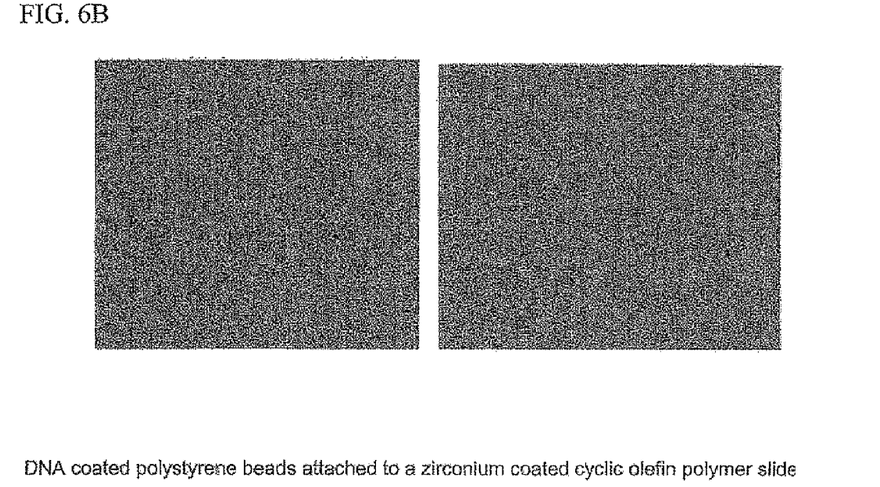

The COP slide readily binds nucleic acid coated polystyrene beads as shown in FIG. 6B, two separate fields of the same slide, indicating surprisingly uniform deposition, deposition on a single plain and immobilization of the beads. This same method is applicable for other metal oxides and other activated surfaces as would be known to one of ordinary skill in the art.

Deposition of Nucleic Acid Ligation Beads Following ePCR onto a Modified Surface Nucleic acid coated polystyrene beads (e.g., Dynal® beads, Invitrogen, Carlsbad, Calif.) (14 µL of 4 million/µL) were washed 3×150 µL 100 mM. NaCl. The beads were resuspended in 160 µL of 100 mM NaCl and sonicated. The zirconium treated slide was loaded into a metal holder equipped with a removable 150 µL chamber for bead deposition. The bead suspension was then pipetted into the 150 µL bead deposition chamber (which was secured to the slide with compression gaskets) and sealed with deposition hole tape seals. The slide was then centrifuged at 180 RCF for five minutes followed by removal from the centrifuge and then incubated at 37° C. for one hour. The seal was removed and an additional 100 mM NaCl was pipetted through the deposition chamber. The removable deposition chamber was separated from the slide and slide holder. The slide was stored in 100 mM NaCl until used in a next-generation (e.g., SOLiD™ instrument, Applied Biosystems, Foster City, Calif.) sequencing instrument.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method of immobilizing a particle onto a surface comprising:

depositing a metal oxide layer onto the surface; and contacting a functionalized particle onto the metal oxide surface, the particle selected from the group consisting of a bead, a refractory bead, and a ligation bead;

wherein the particle is immobilized on the surface.

2. The method of claim 1, wherein the functionalized particle comprises phosphate moieties, carboxylated moieties or a combination thereof.

3. The method of claim 2, wherein the phosphate moieties are derived from phosphodiester linkages selected from the group consisting of a nucleic acid, an oligonucleotide or a biomolecule containing nucleic acids, carboxylates, phosphonates or phosphates.

4. The method of claim 1, wherein the surface is a glass, a metal, a metal oxide or an organic polymer.

5. The method of claim 1, wherein the particle is composed of a material selected from the group consisting of organic polymers, silicate polymers, alumina, titania, zirconia, and combinations thereof.

6. The method of claim 4, wherein the polymer is solid at operating temperatures.

7. The method of claim 4, wherein the polymer is optically transparent.

8. The method of claim , wherein the polymer is stable in a variety of solvent.

9. The method of claim 4, wherein the polymer is activated to comprise transition metal reactive groups.

10. The method of claim 9, wherein the reactive group is selected from hydroxyl, carboxyl, phosphate, phosphonate, silanol, alumina and oxides of transition metals.

11. The method of claim 1, wherein the surface comprises a material selected from the group consisting of silicon, aluminum, germanium, gallium, titanium, tantalum, indium, zirconium, magnesium, tin, gold, silver, hafnium, carbon and an organic polymer derivative.

12. The method of claim 4, wherein the polymer is selected from the group consisting of cyclic olefin polymer (COP), cyclic olefin co-polymer (COC), polypropylene, polycarbonate, fluorinated polyethylene, polymethyl methacrylate, polystyrene, polybutadiene, and blends thereof.

13. The method of claim 12, wherein the blend is a mixture of polystyrene, polypropylene and polybutadiene.

14. The method of claim 1 further comprising passivating the surface.

15. The method of claim 14, wherein the passivating comprises a passivating agent selected from the group consisting of poly(vinyl phosphoric acid), pyrophosphate, poly(acrylic acid), poly(vinyl alcohol), polyethylene glycol comprising functionalities of poly-phosphate-, poly-carboxylate-, or poly-hydroxyl- or combinations thereof and poly(N,N-dimethylacrylamide).

16. The method of claim 1, wherein the metal oxide comprises an organic polymer derivative.

17. A method of immobilizing a particle onto a surface comprising:
   depositing a metal oxide layer onto the surface; and
   contacting a functionalized particle onto the metal oxide surface, the particle being at least 0.5 to 10 microns in size;
   wherein the particle is immobilized on the surface.

18. The method of claim 1, wherein the particle includes an attached nucleic acid, oligonucleotide, or primer.

19. The method of claim 1, wherein the metal oxide layer comprises zirconium.

* * * * *